United States Patent [19]

Mano et al.

[11] Patent Number: 4,871,372
[45] Date of Patent: Oct. 3, 1989

[54] DYE COMPOSITION FOR KERATINOUS FIBER

[75] Inventors: Tsutomu Mano, Saitama; Jiro Kawase, Funabashi; Daisuke Misu, Ichikai; Michio Obayashi, Utsunomiya, all of Japan

[73] Assignee: Kao Corporation, Tokyo, Japan

[21] Appl. No.: 217,776

[22] Filed: Jul. 12, 1988

[30] Foreign Application Priority Data

Jul. 17, 1987 [JP] Japan ................................ 62-178441
Sep. 29, 1987 [JP] Japan ................................ 62-245084
Sep. 29, 1987 [JP] Japan ................................ 62-245085

[51] Int. Cl.$^4$ .................... F16B 23/00; F16B 35/06
[52] U.S. Cl. .......................................... 8/410; 8/416; 8/421; 560/45; 562/452; 564/443
[58] Field of Search .................... 560/45; 562/452; 564/443; 8/410, 416, 424

[56] References Cited

U.S. PATENT DOCUMENTS 4,168,153  9/1979  Pilgram et al. .................... 564/190
4,218,373  8/1980  Wolfrum et al. .................... 260/198

FOREIGN PATENT DOCUMENTS 2176494 12/1986 United Kingdom .

OTHER PUBLICATIONS

Chemical Abstracts, vol. 78, No. 124,183s (1973).
Search Report for European Patent Application 88 111363.3.

Primary Examiner—Paul Lieberman
Assistant Examiner—John F. McNally
Attorney, Agent, or Firm—Oblon, Spivak, McClelland, Maier & Neustadt

[57] ABSTRACT

A dye composition for keratinous fibers comprising a specific type of trifluoromethylated aniline derivative, as a developer, and a coupling substance is disclosed. The composition provides high degree of saturation and vividness of colors as well as good fastness. Dyeing with the use of the dye composition ensures a variety of developer-coupling agent combinations, which can provide a wide variety of colors with a high degree of color saturation and vividness. The color produced possesses excellent light resistance, washing resistance, and wear resistance. Among the trifluoromethylated aniline derivative, used as a developer, a p-phenylenediamine-type trifluoromethylated aniline derivative of the following formula is a novel compound.

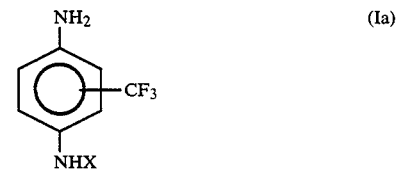

(Ia)

in which X represents a specific type of mono- or polyhydroxyalkyl group, alkyl group, or other organic group.

2 Claims, No Drawings

DYE COMPOSITION FOR KERATINOUS FIBER

BACKGROUND OF THE INVENTION

1. Field of the Invention

This invention relates to a dye composition for keratinous fibers, and, more particularly, to a dye composition for keratinous fibers which is capable of dyeing keratinous fibers such a hairs and the like at a high degree of saturation and vividness, and to a p-phenylenediamine derivative useful as a developer when formulated into such a dye composition. The invention also is directed to a process for preparing the p-phenylenediamine derivatives.

2. Description of the Background

Oxidizing dyes, in which a developer and a coupling agent are employed in combination, have widely been used for dyeing keratinous fibers such as hairs or the like. These oxidizing dyes make use of the strong dyeing capability of oxidizing coloring substances which are produced by the oxidizing-coupling reaction of a developer and a coupling agent. Para-phenylenediamine derivatives, diaminopyridine derivatives, 4-aminopyrazolone derivatives, hetero-cyclic hydrazone, and the like are used as the developer.

These conventional oxidizing dyes have defects in their performance which are yet to be satisfied in terms of saturation or vividness of colors, dyeing capability, and fastness. Development of a dye which is free from these defects has, therefore, been desired.

Performance of an oxidizing dye such as saturation or vividness of colors, dyeing capability, fastness, and the like is greatly dependent upon the characteristics of the developer used. It is, therefore, very important in eliminating the above defects of oxidizing dyes to find a developer possessing an excellent characteristics.

The present inventors have undertaken extensive studies in order to overcome the above problems in oxidizing dyes, and as a result found that use of a trifluoromethylated aniline derivative for dyeing keratinous fibers provides a high degree of saturation and vividness of colors as well as good fastness. This finding has led to the completion of this invention.

SUMMARY OF THE INVENTION

Accordingly an object of this invention is to provide a dye composition for keratinous fibers comprising a developer and a coupling substance, wherein said developer is a trifluoromethylated aniline derivative represented by the following formula (I) or a salt thereof:

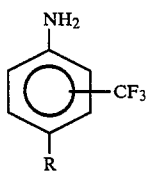
(I)

in which R represents a hydroxyl group or a group represented by—NHR', wherein R' represents a $C_{2-6}$ mono- or polyhydroxyalkyl group, a $C_{1-20}$ alkyl group, or a group represented by —$(CH_2)_n$—O—R'', [wherein R'' stands for a $C_{1-4}$ alkyl group, a $C_{1-4}$ mono- or polyhydroxyalkyl group, a group represented by —$(CH_2)_n$—$NR^3R^4$ (wherein $R^3$ and $R^4$ may be same or different and denote hydrogen atoms, $C_{1-20}$ alkyl groups, or $C_{2-6}$ mono- or polyhydroxyalkyl groups, and n denotes an integer of 1 to 4), or —$(CH_2)_n$—$COOR^5$ (wherein R'' is a hydrogen atom, a $C_{1-4}$ alkyl group, or a $C_{2-6}$ mono- or polyhydroxyalkyl group, and n denotes an integer of 1 to 4), and n denotes an integer of 1 to 4].

Another object of this invention is to provide a novel p-phenylenediamine derivative represented by the following formula (Ia) or a salt thereof:

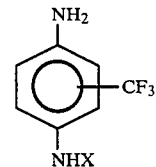
(Ia)

in which X represents a $C_{1-4}$ mono- or polyhydroxyalkyl group, a $C_{1-20}$ alkyl group, or a group represented by —$(CH_2)_n$—O—R'', [wherein R'' stands for a $C_{1-4}$ alkyl group, a $C_{1-4}$ mono- or polyhydroxyalkyl group, a group represented by —$(CH_2)_n$—$NR^3R^4$ (wherein $R^3$ and $R^4$ may be same or different and denote hydrogen atoms, $C_{1-20}$ alkyl groups, or $C_{2-6}$ mono or polyhydroxyalkyl groups, and n denotes an integer of 1 to 4), or —$(CH_2)_n$—$COOR^5$ (wherein $R^5$ is hydrogen atom, a $C_{1-6}$ alkyl group, or a $C_{2-6}$ mono- or polyhydroxyalkyl group, and n denotes an integer of 1 to 4), and n denotes an integer of 1 to 4].

Still another object of this invention is to provide a process for preparing the above novel p-phenylenediamine derivative the formula (Ia) or a salt thereof, which comprises reducing a compound represented by the following formula (II):

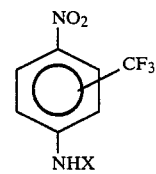
(II)

in which X has the same meaning as defined for the formula (Ia).

Other objects, features and advantages of the invention will hereinafter become more readily apparent from the following description.

DETAILED DESCRIPTION OF THE INVENTION AND PREFERRED EMBODIMENTS

Among trifluoromethylated aniline derivatives, p-phenylenediamine derivatives represented by the following formula (Ia) or the salts thereof are novel compounds.

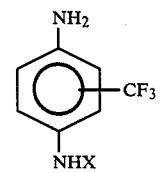
(Ia)

in which X represents a $C_{2-6}$ mono- or polyhydroxyalkyl group, a $C_{1-20}$ alkyl group, or a group represented by —$(CH_2)_n$—O—R'', [wherein R'' stands for a $C_{1-4}$ alkyl group, a $C_{1-4}$ mono- or polyhydroxyalkyl group, a group represented by —$(CH_2)_n$—$R^3R^{4''}$ (wherein $R^3$ and $R^4$ may be same or different and denote hydrogen atoms, $C_{1-20}$ alkyl groups, or $C_{2-6}$ mono- or polyhydroxyalkyl groups, and n denotes an integer of 1 to 4), or —$(CH_2)_n$—$COOR^5$ (wherein R″ is a hydrogen atom, a $C_{1-6}$ alkyl group, or a $C_{2-6}$ mono- or polyhydroxyalkyl group, and n denotes an integer of 1 to 4), and n denotes an integer of 1 to 4].

The p-phenylenediamine derivative of formula (Ia) can be prepared, for example, by reducing the compound (II) according to the following reaction scheme:

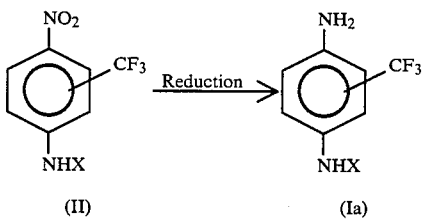

The compound (II) can be prepared, for example, by the reaction of the chlorinated compound of the formula (III) and mono- or polyhydroxyalkylamine of the formula (IV).

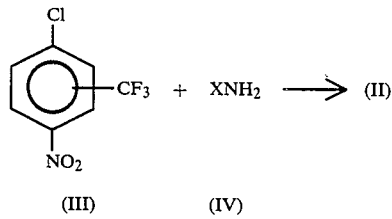

This reaction may be carried out according to the method described in *Arzneim. Forsch.*, 25, 681 (1975).

The reduction of the compound of formula (II) may be carried out according to the conventional reduction of a nitro group. A simple and effective method, however, is a catalytic hydrogenation or reduction in the presence of zinc under alkaline conditions.

Palladium, platinum, copper, nickel, or the like are used for the catalytic hydrogenation. A solvent such as methanol, ethanol, ethyl acetate, dimethylformamide, or the like is desirably used in the reaction. The reaction temperature is in the range between room temperature and the boiling point of the solvent used, and the pressure may be 1 to 250 kg/cm². Upon completion of the reaction, the catalyst is removed by filtration. After condensation of the filtrate, purification can be performed very easily by evaporating the solvent or recrystallizing the target compound.

Reduction using zinc is carried out by heating the raw materials under reflux in an aqueous solution of alkali such as sodium hydroxide, potassium hydroxide, or the like in the presence of an excess amount of zinc, and adding to the reaction system, as required, a solvent dissolvable in water such as methanol, ethanol, acetone, N,N-dimethylformamide, dimethylsulfoxide, or the like. Upon completion, solid substances are removed by filtration, and the filtrate is extracted with a suitable solvent and condensed. The condensate thus obtained can be easily purified by evaporating the solvent or recrystallizing the target compound.

The compound of this invention of formula (Ia) thus prepared can be converted according to a conventional method into a salt by reaction of this compound with an organic or inorganic acid such as hydrochloric acid, sulfuric acid, phosphoric acid, acetic acid, propionic acid, lactic acid, citric acid, or the like.

Compounds of formula (I), other than those of formula (Ia) which is novel in the art, can be prepared by reducing p-nitrophenol or p-nitroaniline trifluoromethylated according to the process which was discussed just above in connection with the process for preparing the compound of formula (Ia). More specifically, trifluoromethylated p-aminophenol is prepared by the method described in *J. Org. Chem.*, 27, 4460 (1962), and trifluoromethylated p-phenylenediamine is prepared by the method described in *J. Ind. Chem.*, 69, 2229, (1966), for example.

Given as particularly preferable examples of trifluoromethylated aniline derivatives of formula (I) are 4-(2'-hydroxyethyl)amino-3-trifluoromethylaniline, 4-(2'-hydroxyethyl)amino-2-trifluoromethylaniline, 4-(2',3'-dihydroxypropyl)amino-3-trifluoromethylaniline, 1,4-diamino-2-trifluoromethylbenzene, 4-hydroxy-2trifluoromethylaniline, 4-hydroxy-3-trifluoromethylaniline, 4-(3,-hydroxypropyl)amino-3-trifluoromethylaniline, 4-(2,-hydroxypropyl)amino-3-trifluoromethylaniline, 4-n-butylamino-3-trifluoromethylaniline, 4-sec-butylamino-3-trifluoromethylaniline, 4-n-dodecylamino-3-trifluoromethylaniline, 4-(2,-methoxyethyl)amino-3-trifluoromathylaniline, 4-[2'-(2''-hydroxyethoxy)ethyl]amino-3-trifluoromethylaniline 1-N(2'-aminoethyl)amino-2-trifluoromethyl-4-aminobenzene, 1-N-(2'-dimethylaminoethyl)amino-2-trifluoromethyl-4-aminobenzene, and 1-N-(2'-carboxyethyl)amino-2-trifluoromethyl-4-aminobenzene. Preferable salts of these trifluoromethylated aniline derivatives are salts of these derivatives of an organic or inorganic acid such as hydrochloric acid, sulfuric acid, phosphoric acid, acetic acid, propionic acid, lactic acid, citric acid, and the like.

There is no specific restriction as to the coupling agent to be used in the dye composition of this invention. Any conventionally used coupling agent can be used for the purpose of this invention. Examples are 5-amino-o-cresol, α-naphthol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, hydroquinone, 2,4-diaminoanisole, m-toluylenediamine, 4-aminophenol, resorcin, resorcinmonomethylether, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethyl-amino-4-hydroxy-2 1-amino-3-acetyl-acetamino-4-nitrobenzole, 1-amino-3-cyanacetyl-amino-4-nitrobenzole, m-aminophenol, 4-chlororesorcin, 2-methylresorcin, 2,4-diaminophenoxyethanol, 2,6-diaminopyridine, 2,4-diaminofluorobenzene, 3,5-diamino-fluorobenzene, 3,5-diaminotrifluoromethylbenzene, 2,4-diamino-6-hydroxypyrimidine, 2,4,6-triamino-pyrimidine, 2-amino-4,6-dihydroxypyrimidine, 4-amino-2,6-dihydroxypyrimidine, 4,6-diamino-2-hydroxypyrimidine, p-nitro-o-phenylenediamine, p-nitro-m-phenylenediamine, 2-amino-5-nitrophenol, o-nitro-p-phenylenediamine, 2-amino4-nitrophenol, and the like. Among these, 5-amino-o-cresol and α-naphthol are desirable for producing a vivid red color, and m-phenylenediamine is effective in obtaining a blue color with a high degree of saturation.

The proportion of the developer and the coupling agent to be formulated into the dye composition of this invention is approximately in the range of 1:0.5 to 1:2 in molar ratio. Excessive use of one component to the other is allowable in this range. One type of developer and coupling agent can be employed either independently or in combination with one or more other types of developers or coupling agents.

In addition to the above-mentioned developers or coupling agents, any known developers, conventional direct dyes, or the like compounds can be formulated to the composition of this invention, if necessary for producing a desired color.

Hairs or other objects are colored by the dye composition of this invention through an oxidizing coupling reaction of the components with the aid of oxygen in the air, when the dye composition is applied to the object to be dyed. Effecting the oxidizing coupling reaction with the aid of a chemical oxidizing agent, however, is more desirable. Especially preferable oxidizing agents are hydrogen peroxide, hydrogen peroxide-adduct of urea, melamine, or sodium borate, or a mixture of one of these hydrogen peroxide-adducts and potassium peroxide-disulfate, and the like.

It is usually desirable to provide the dye composition of this invention in the form of either a cream, emulsion, gel, solution, or the like. Preparing the composition in such forms can be performed according to the conventional method. In this instance, in addition to the developers and coupling agents, various ingredients which are commonly used in cosmetics are formulated into the composition. Such ingredients include wetting agents (emulsifiers), solubilizing agents, viscosity increasing agents, stabilizers, tactile sence improvers, hair conditioning base components, perfumes, and the like. Wetting agents (emulsifiers) used in the composition include, for example, alkylbenzenesulfonates, fatty alcohol sulfates, alkylsulfonates, fatty acid alkanolamides, ethylene oxide adducts of fatty alcohol, and the like. Given as examples of viscosity increasing agents are methyl cellulose, starch, higher fatty alcohols, paraffin oils, fatty acids, and the like. Examples of stabilizers include reducing agents such as sulfites, hydroquinone derivatives, chelating agents, and the like. Tactile sence improvers and hair conditioning base components are typified by silicones, higher alcohols, various kinds of nonionic surface active agents and cationic polymers, and the like.

The amounts of the developers plus coupling agents to be formulated into the abovementioned form of the invented composition are 0.2 to 5% by weight, and preferably 1 to 3% by weight. The desirable amount of the wetting agents (emulsifiers) and viscosity increasing agents in the composition is usually 0.5 to 30% by weight and 0.1 to 25% by weight, respectively.

It is desirable that the overall pH of the composition be adjusted to the range of 8 to 10.

A typical procedure for dyeing keratinous fibers using the dye composition of this invention is now illustrated. A dye fluid is first prepared by adding an oxidizing agent to the dye composition to effect oxidizing coupling of the mixture. This dye fluid is applied to the subject keratinous fibers, which are then allowed to stand for about 10 to 50 minutes, preferably 25 to 35 minutes to effect action of the dye onto the fibers. The keratinous fibers thus sufficiently dyed are finally washed and dried. It is desirable that the temperature of the dye fluid be maintained between 15° to 45° C.

Dyeing with the use of the dye composition according to the present invention ensures a variety of developer coupling agent combinations, which can provide a wide variety of colors ranging from yellow, red, blue through gray or charcoal with a high degree of color saturation and vividness. In addition, the color produced possesses excellent light resistance, washing resistance, and wear resistance.

Other features of the invention will become apparent in the course of the following description of the exemplary embodiments which are given for illustration of the invention and are not intended to be limiting thereof.

EXAMPLES

Reference Example 1

Synthesis of 1-N-(2,-hydroxyethyl)amino-2-trifluoromethyl-4-nitrobenzene:

A mixture of 13.53 g (0.06 mol) of 1-chloro-2-trifluoromethyl-4-nitrobenzene and 8.06 g (0.132 mol) of ethanolamine was stirred under heating at 100°–120° C. for 5 hours. A yellow solid substance deposited in the reaction mixture by the addition of water thereinto was collected by filtration, washed with water, and dried. This substance was recrystallized from chloroform to produce 10.16 g of 1-N-(2,-hydroxyethyl)amino-2-trifluoromethyl-4-nitrobenzene at a yield of 69%.

Melting Point: 86°–87° C. [88° C. in literature (*Arzneim. Forsch.*, 25, 681 (1975)]

Reference Examples 2-17

The compounds listed in Table 1 were prepared in the same manner as in Reference Example 1.

TABLE 1

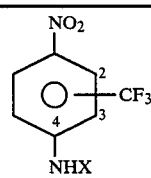

(II)

| Reference Example | X | Position of $CF_3$ | Yield (%) | Melting Pt. or Boiling Pt. | Elemental Analysis | C | H | N |
|---|---|---|---|---|---|---|---|---|
| 2 | —CH$_2$CH(CH$_3$)OH | 3 | 91 | 62–63° C. (m.p.) | Found | 45.71 | 4.50 | 10.81 |
|   |   |   |   |   | Calculated | 45.46 | 4.20 | 10.60 |
| 3 | —CH$_2$CH$_2$CH$_2$OH | 3 | 97 | 79–82° C. (m.p.) | Found | 45.22 | 4.28 | 10.32 |
|   |   |   |   |   | Calculated | 45.46 | 4.20 | 10.60 |
| 4 | —CH$_2$CH(OH)CH$_2$OH | 3 | 76 | 99–102° C. | Found | 42.91 | 3.81 | 9.92 |

TABLE 1-continued

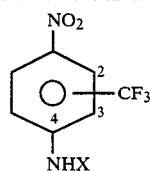

(II)

| Reference Example | X | Position of CF$_3$ | Yield (%) | Melting Pt. or Boiling Pt. | Elemental Analysis | C | H | N |
|---|---|---|---|---|---|---|---|---|
| 5 | —CH$_2$CH$_2$OH | 2 | 48 | (m.p.) 106–109° C. | Calculated Found | 42.87 43.33 | 3.96 3.81 | 10.00 11.21 |
| 6 | —CH$_2$CH(CH$_3$)OH | 2 | 47 | (m.p.) 104–106° C. | Calculated Found | 43.21 45.31 | 3.63 4.29 | 11.20 10.48 |
| 7 | —CH$_2$CH$_2$CH$_2$OH | 2 | 53 | (m.p.) 106–109° C. | Calculated Found | 45.46 45.58 | 4.20 4.26 | 10.60 10.87 |
| 8 | —CH$_2$CH(OH)CH$_2$OH | 2 | 42 | (m.p.) 96–99° C. | Calculated Found | 45.46 42.52 | 4.20 3.99 | 10.60 9.89 |
| 9 | —CH$_2$CH$_2$CH$_2$CH$_3$ | 3 | 85 | (m.p.) 110° C./0.15 mmHg (b.p.) | Calculated Found Calculated | 42.87 50.42 50.38 | 3.96 5.03 5.00 | 10.00 10.91 10.68 |
| 10 | —CHCH$_2$CH$_3$<br>\|<br>CH$_3$ | 3 | 87 | 105° C./0.20 mmHg (b.p.) | Found Calculated | 50.61 50.38 | 5.01 5.00 | 10.43 10.68 |
| 11 | —(CH$_2$)$_5$CH$_3$ | 3 | 80 | 130° C./0.15 mmHg (b.p.) | Found Calculated | 54.01 53.79 | 5.99 5.90 | 9.72 9.65 |
| 12 | —(CH$_2$)$_{11}$CH$_3$ | 3 | 67 | 180° C./0.10 mmHg (b.p.) | Found Calculated | 60.22 60.95 | 7.48 7.81 | 7.16 7.48 |
| 13 | —CH$_2$CH$_2$OCH$_2$CH$_2$OH | 3 | 86 | 49–51° C. (m.p.) | Found Calculated | 44.99 44.90 | 4.48 4.45 | 9.53 9.52 |
| 14 | —CH$_2$CH$_2$OCH$_3$ | 3 | 88 | 77–79° C. (m.p.) | Found Calculated | 45.52 45.46 | 4.25 4.19 | 10.81 10.60 |
| 15 | —CH$_2$CH$_2$COOH | 3 | 81 | 118.5–120.5° C. (m.p.) | Found Calculated | 43.31 43.17 | 3.42 3.26 | 10.55 10.07 |
| 16 | —CH$_2$CH$_2$NH$_2$ | 3 | 86 | 89.2–91.6° C. (m.p.) | Found Calculated | 43.31 43.38 | 4.61 4.33 | 16.53 16.86 |
| 17 | —CH$_2$CH$_2$NMe$_2$ | 3 | 84 | 83.3–85.0° C. (m.p.) | Found Calculated | 47.22 47.65 | 5.31 5.09 | 20.00 15.16 |

Example 1

Synthesis of 4-(2,-hydroxyethyl)amino-3-trifluoromethylaniline:

(1) Synthesis via catalytic reduction

Into 150 ml of ethanol was dissolved 10 g (0.04 mol) of 1-N-(2'-hydroxyethyl)amino-2-trifluoromethyl-4-nitrobenzene. To the mixture 1 g of palladium on charcoal was added, and theoretically equivalent amount of hydrogen was charged at normal temperature and pressure. Catalyst was removed from the reaction mixture by filtration and the filtrate was condensed to produce a solid material. Through recrystallization from carbon tetrachloride 7.48 g of 4-(2,-hydroxyethyl)amino-3-trifluoromethylaniline was obtained at a yield of 85%.

(2) Synthesis via reduction using zinc

To 9.48 g (0.038 mol) of 1-N-(2,-hydroxyethyl)amino-2-trifluoromethyl-4-nitrobenzene were added 11 g of zinc powder, 5 ml of 20% sodium hydroxide and 20 ml of ethanol and the mixture was heated under reflux for 2 hours. After the zink powder was removed from the reaction mixture by filtration, water was added to the filtrate followed by extraction with ethyl acetate. The organic phase obtained was dried over salt cake and codensed to produce a solid material, which was then recrystallized from carbon tetrachloride to obtain 7.16 g of 4-(2,-hydroxyethyl)amino-3-trifluoro ethylaniline at a yield of 86%.

Melting point: 74–75° C.

Elemental analysis: Found C: 49.29 , H: 5.21 , N: 12.97 Calculated C: 49.09 , H: 5.04 , N: 12.72

Examples 2-17

The compounds listed in Table 2 were prepared in the same manner as in Example 1.

TABLE 2

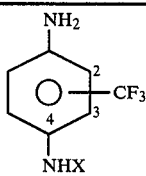

(Ia)

| Reference Example | X | Position of CF$_3$ | Yield* (%) | Melting Pt. or Boiling Pt. | | Elemental Analysis | | |
|---|---|---|---|---|---|---|---|---|
| | | | | | | C | H | N |
| 2 | —CH$_2$CH(CH$_3$)OH | 3 | 82 | 91–93° C. (m.p.) | Found Calculated | 51.36 51.24 | 5.71 5.59 | 11.81 11.96 |
| 3 | —CH$_2$CH$_2$CH$_2$OH | 3 | 85 | 88–90° C. (m.p.) | Found Calculated | 51.22 51.24 | 5.57 5.59 | 11.90 11.96 |
| 4 | —CH$_2$CH(OH)CH$_2$OH | 3 | 94 | 114–115° Found (m.p.) | Calculated | 47.92 48.00 | 5.01 5.24 | 11.03 11.20 |
| 5 | —CH$_2$CH$_2$OH | 2 | 75 | 47–48° C. (m.p.) | Found Calculated | 49.31 49.09 | 5.21 5.04 | 12.99 12.72 |
| 6 | —CH$_2$CH(CH$_3$)OH | 2 | 87 | 53–55° C. (m.p.) | Found Calculated | 51.33 51.24 | 5.80 5.59 | 12.09 11.96 |
| 7 | —CH$_2$CH$_2$CH$_2$OH | 2 | 86 | oil** | Found Calculated | 51.31 51.24 | 5.50 5.59 | 11.91 11.96 |
| 8 | —CH$_2$CH(OH)CH$_2$OH | 2 | 75 | 89–92° C. (m.p.) | Found Calculated | 47.81 48.00 | 5.22 5.24 | 11.48 11.20 |
| 9 | —CH$_2$CH$_2$CH$_2$CH$_3$ | 3 | 63 | 88° C./0.15 mmHg (b.p.) | Found Calculated | 56.88 56.89 | 6.52 6.51 | 12.38 12.05 |
| 10 | —CHCH$_2$CH$_3$<br>\|<br>CH$_3$ | 3 | 77 | 75° C./0.1 mmHg (b.p.) | Found Calculated | 56.66 56.89 | 6.38 6.51 | 12.17 12.06 |
| 11 | —(CH$_2$)$_5$CH$_3$ | 3 | 72 | 103° C./0.15 mmHg (b.p.) | Found Calculated | 59.76 59.99 | 7.32 7.36 | 10.21 10.76 |
| 12 | —(CH$_2$)$_{11}$CH$_3$ | 3 | 89 | 140° C./0.10 mmHg (b.p.) | Found Calculated | 65.98 66.25 | 9.21 9.07 | 8.44 8.13 |
| 13 | —CH$_2$CH$_2$OCH$_2$CH$_2$OH | 3 | 73 | oil** | Found Calculated | 51.12 50.00 | 5.86 5.72 | 10.41 10.60 |
| 14 | —CH$_2$CH$_2$OCH$_3$ | 3 | 75 | 90° C./0.15 mmHg (b.p.) | Found Calculated | 51.62 51.28 | 5.82 5.59 | 11.68 11.96 |
| 15 | —CH$_2$CH$_2$COOH | 3 | 85*** | 129.2–130.6° C. (m.p.) | Found Calculated | 48.16 48.39 | 4.40 4.47 | 11.38 11.29 |
| 16 | —CH$_2$CH$_2$NH$_2$ | 3 | 82 | 105° C.(0.15 mmHg) (b.p.) | Found Calculated | 49.35 49.30 | 5.58 5.51 | 20.00 19.17 |
| 17 | —CH$_2$CH$_2$NMe$_2$ | 3 | 84 | 102° C.(0.1 mmHg) (b.p.) | Found Calculated | 53.51 53.42 | 6.82 6.52 | 17.02 16.99 |

*yield when zinc was used as a reducing catalyst
**purified by silica gel column chromatography after reduction
***the reducing yield by Pd-C

Example

Preparation and Evaluation of the Inventive Compositions

| Base components: | |
|---|---|
| oleic acid | 10% |
| diethanolamide oleate | 8% |
| oleyl alcohol | 2% |
| polyoxyethyleneoctyl-dodecylether (Average EO mols: 20) | 10% |
| ethanol | 15% |
| propylene glycol | 10% |
| ammonium chloride | 3% |
| 25% aqueous ammonium | 7% |
| water | 35% |

Into 100 g of the above base components 0.01 mol of the developer Table 3 and 0.01 mol of the coupling agent listed in Table 4 were mixed. The mixture was then adjusted to pH 9.5 with ammonia to produce the dye composition of this invention.

To 100 g of the dye composition of this invention an equivalent weight of 6% aqueous hydroperoxide solution was added to prepared a dye solution. This dye solution was applied to a gray human hair, which was left at 30° C. for 30 minutes. The hair was subsequently washed with a normal shampoo and dried. Table 5 shows the observed color tone of the dyed hair.

TABLE 3

| | Developers |
|---|---|
| P1 | 4-(2'-hydroxyethyl)amino-3-trifluoromethylaniline |
| P2 | 4-(2'-hydroxyethyl)amino-2-trifluoromethylaniline |
| P3 | 4-(2',3'-dihydroxypropyl)amino-3-trifluoromethylaniline |
| P4 | 1,4-diamino-2-trifluoromethylbenzene |
| P5 | 4-hydroxy-2-trifluoromethylaniline |
| P6 | 4-hydroxy-3-trifluoromethyl-aniline |
| P7 | 4-sec-butylamino-3-trifluoromethylaniline |
| P8 | 4-n-butylamino-3-trifluoromethylaniline |
| P9 | 4-n-dodecylamino-3-trifluoromethylaniline |
| P10 | 4-(2'-methoxyethyl)amino-3-trifluoromethylaniline |

TABLE 4

| | Coupling Agents |
|---|---|
| C1 | m-phenylenediamine |
| C2 | resorcin |
| C3 | m-aminophenol |
| C4 | p-amino-o-cresol |
| C5 | α-naphthol |
| C6 | m-phenylenediamine |
| C7 | resorcin |

TABLE 4-continued

| Coupling Agents | |
| --- | --- |
| C8 | m-aminophenol |
| C9 | 5-amino-o-cresol |

TABLE 5

| Composition Nos. | Developers | Coupling agents | Color tone |
| --- | --- | --- | --- |
| 1 | P 1 | C 1 | blue |
| 2 | P 1 | C 2 | brown |
| 3 | P 1 | C 3 | brown-black |
| 4 | P 1 | C 4 | red |
| 5 | P 1 | C 5 | purplish red |
| 6 | P 2 | C 1 | grayish green |
| 7 | P 2 | C 2 | pale yellow |
| 8 | P 2 | C 3 | red |
| 9 | P 2 | C 4 | purplish red |
| 10 | P 2 | C 5 | blue |
| 11 | P 3 | C 1 | blue |
| 12 | P 3 | C 2 | brown |
| 13 | P 3 | C 3 | brown-black |
| 14 | P 3 | C 4 | red |
| 15 | P 3 | C 5 | purplish red |
| 16 | P 4 | C 6 | blue |
| 17 | P 4 | C 7 | green |
| 18 | P 4 | C 8 | liver color |
| 19 | P 4 | C 9 | red |
| 20 | P 5 | C 6 | brown |
| 21 | P 5 | C 7 | ivory |
| 22 | P 5 | C 8 | yellowish orange |
| 23 | P 5 | C 9 | orange |
| 24 | P 6 | C 6 | light brown |
| 25 | P 6 | C 7 | ivory |
| 26 | P 6 | C 8 | light brown |
| 27 | P 6 | C 9 | orange |
| 28 | P 7 | C 1 | green |
| 29 | P 7 | C 2 | cream |
| 30 | P 7 | C 4 | orange |
| 31 | P 7 | C 5 | purplish red |
| 32 | P 8 | C 4 | orange |
| 33 | P 8 | C 5 | violet |
| 34 | P 9 | C 4 | cream |
| 35 | P 9 | C 5 | light purple |
| 36 | P 10 | C 4 | orange |
| 37 | P 10 | C 5 | violet |

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. A dye composition for keratinous fibers comprising a developer and a coupling substance, wherein said developer is a trifluoromethylated aniline derivative represented by the following formula (I) or a salt thereof:

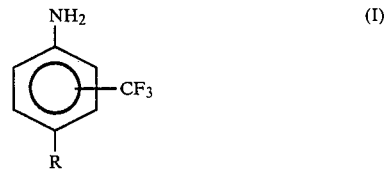

in which R represents a hydroxyl group or a group represented by —NHR', wherein R' represents a $C_{2-6}$ mono- or polyhydroxyalkyl group, a $C_{1-20}$ alkyl group, or a group represented by —$(CH_2)_n$—O—R", [wherein R" stands for a $C_{1-4}$ alkyl group, a $C_{1-4}$ mono- or polyhydroxyalkyl group, a group represented by —$(CH_2)_n$—O—R", (wherein $R^3$ and $R^4$ may be same or different and denote hydrogen atoms, $C_{1-20}$ alkyl groups, or $C_{2-6}$ mono- or polyhydroxyalkyl groups, and n denotes an integer of 1 to 4), or —$(CH_2)_n$—$COOR^5$ (wherein $R^5$ is a hydrogen atom, a $C_{1-6}$ alkyl group, or a $C_{2-6}$ mono- or polyhydroxyalkyl group, and n denotes an integer of 1 to 4), and n denotes an integer of 1 to 4].

2. The dye composition for keratinous fibers as claimed in claim 1, wherein said trifluoromethylated aniline derivative is a member selected from the group consisting of 4-(2,-hydroxyethyl)amino-3-trifluoromethylaniline, 4-(2'-hydroxyethyl)amino-2-trifluoromethylaniline, 4-(2', 3'-dihydroxypropyl)amino-3-trifluoromethylaniline, 1,4-diamino-2-trifluoromethlbenzene, 4-hydroxy-2-trifluoromethylaniline, 4-hydroxy-3-trifluoromethylaniline, 4-(3'-hydroxypropyl)amino-3-trifluoromethylaniline, 4-(2'-hydroxypropyl)amino-3-trifluoromethylaniline, 4-n-butylamino-3-trifluoromethylaniline, 4-sec-butylamino-3-trifluoromethylaniline, 4-n-dodecylamino-3-trifluoromethylaniline, 4-(2'-methoxyethyl)amino-3-trifluoromethylaniline, and 4-[2'-(2"-hydroxyethoxy)ethyl]amino-3-trifluoromethylaniline.

* * * * *

UNITED STATES PATENT AND TRADEMARK OFFICE
CERTIFICATE OF CORRECTION

PATENT NO. : 4,871,372
DATED : October 3, 1989
INVENTOR(S) : TSUTOMU MANA ET AL

It is certified that error appears in the above-identified patent and that said Letters Patent is hereby corrected as shown below:

Column 1, line 65, "group" should read --group, and n denotes an integer of 1 to 4]--.

Column 2, line 4, "), and n denotes an integer of 1 to 4]." should read --).--;

line 20, "polyhydroxyalkyl group," should read --polyhydroxyalkyl group, and n denotes an integer of 1 to 4],--;

lines 27 and 28, "), and n denotes an integer of 1 to 4]." should read --).--; and line 68, "polyhydroxyalkyl group," should read --polyhydroxyalkyl group, and n denotes an integer of 1 to 4],--.

Column 3, line 1, "$-(CH_2)_n-R^3R^4$" should read --$(CH_2)_n-NR^3R^4$--;

line 5, "(wherein R" " should read --(wherein $R^5$--; and

UNITED STATES PATENT AND TRADEMARK OFFICE
CERTIFICATE OF CORRECTION

PATENT NO. : 4,871,372
DATED : October 3, 1989
INVENTOR(S) : TSUTOMU MANA ET AL

Page 2 of 2

It is certified that error appears in the above-identified patent and that said Letters Patent is hereby corrected as shown below:

lines 7 and 8, "(, and n denotes an integer of 1 to 4]." should read --).--.

Column 12:
    Claim 1, line 6 after formula (I), "group," should read --group, and n denotes and integer of 1 to 4],--;

line 7 after formula (I), "-$(CH_2)_n$-O-R" " should read -- -$(CH_2)_n$-$NR^3R^4$--.

lines 13 and 14 after formula (1), "), and n denotes an integer of 1 to 4]." should read --).--.

Signed and Sealed this

Twenty-seventh Day of October, 1992

Attest:

DOUGLAS B. COMER

*Attesting Officer*      *Acting Commissioner of Patents and Trademarks*